US00PP14150P39

(12) United States Plant Patent
Matsukizono

(10) Patent No.: US PP14,150 P3
(45) Date of Patent: Sep. 16, 2003

(54) PORTULACA PLANT NAMED 'KAKEGAWA CY1'

(75) Inventor: Hiromi Matsukizono, Matsumoto (JP)

(73) Assignee: Sakata Seed Corporation, Yokohama (JP)

( * ) Notice: Subject to any disclaimer, the term of this patent is extended or adjusted under 35 U.S.C. 154(b) by 0 days.

(21) Appl. No.: 10/058,404

(22) Filed: Jan. 30, 2002

(65) Prior Publication Data

US 2003/0145360 P1 Jul. 31, 2003

(51) Int. Cl.[7] ..... A01H 5/00

(52) U.S. Cl. ..... Plt./360

(58) Field of Search ..... Plt./263

*Primary Examiner*—Bruce R. Campell
*Assistant Examiner*—June Hwu
(74) *Attorney, Agent, or Firm*—Jondle & Associates P.C.

(57) ABSTRACT

Portulaca 'Kakegawa CY1' is a new variety of *Portulaca oleracea*. This plant has a vigorous, spreading plant growth which produces unique yellow and orange bi-colored flowers.

1 Drawing Sheet

Genus and species: *Portulaca oleracea*.
Variety denomination: 'Kakegawa CY1'.

BACKGROUND OF THE NEW PLANT

This invention relates to a new and distinct cultivar of Portulaca plant, hereinafter referred to by the name 'Kakegawa CY1'. Portulaca 'Kakegawa CY1' is a new variety of *Portulaca oleracea*. The plant has a vigorous spreading growth habit and can be used as a groundcover. It can also be used in a potted or hanging basket presentation. The invention's flowers are a unique yellow and orange bicolor. The flowers are single and measure approximately 3.5 centimeters in diameter when fully open. The plant performs well in hot and dry climates. The plant is very resistant to rain, heat and drought.

ORIGIN AND ASEXUAL REPRODUCTION

The new cultivar is propagated asexually from vegetative cuttings. The asexual reproduction establishes that the plant does in fact maintain the characteristics described in successive generations. 'Kakegawa CY1' has been reproduced by stem cuttings in Salinas, Calif., and all of the characteristics thereof have been determined to be firmly fixed.

In June, 1998 the breeder identified a sport from the variety 'Summer Baby Orange' (not patented) that possessed orange petals with yellow patches along the margin. The selection was made in the breeder's greenhouse in Kagoshima, Japan. The new variety was isolated by vegetative propagation. In April, 1999 and again in September, 1999 the new variety was vegetatively propagated and all progeny were found stable and uniform.

BRIEF DESCRIPTION OF DRAWINGS

The accompanying drawings serve by color photographic means to illustrate the new plant variety, 'Kakegawa CY1'. The colors are represented as true as possible using conventional photographic procedures.

DETAILED DESCRIPTION OF THE NEW VARIETY

Figure 2:
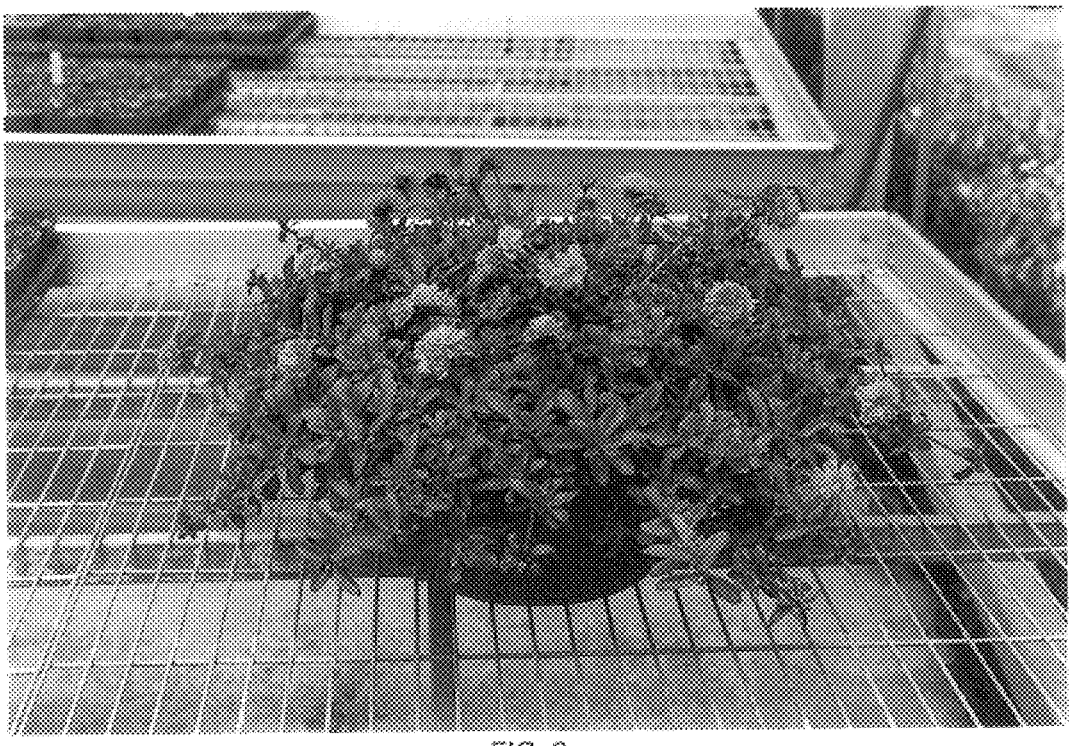
FIG. 2 is a view of several plants of the new cultivar growing in a 35.0 cm diameter pot.
Figure 1:
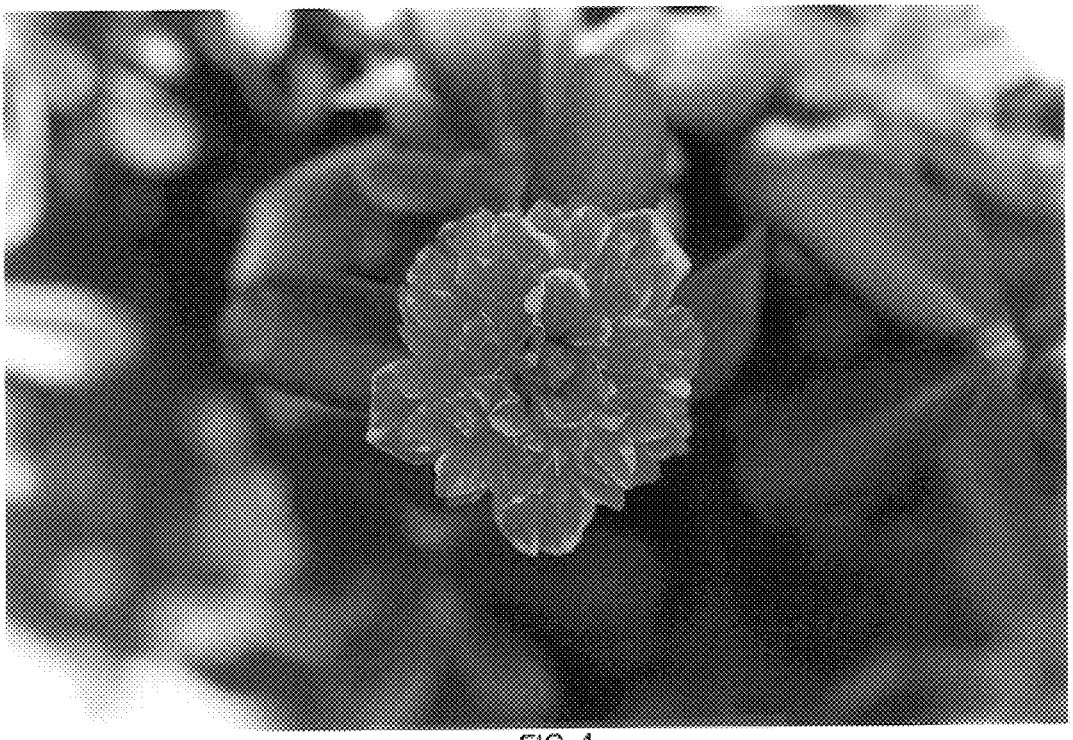
FIG. 1 is a close-up view of a 'Kakegawa CY1' flower illustrating its color and shape.

The following description is based on observations and measurements from 14–16 week old plants grown in 15 cm pots at Salinas, Calif. Plants were propagated from vegetative cuttings and grown in a glass greenhouse. These plants were grown in plastic pots containing a peat moss-based medium. Soluble fertilizer containing 18% nitrogen, 8% phosphorus and 18% potassium were applied every fourth irrigation. The plants were typically watered twice per week. Pots were topdressed with a slow release fertilizer containing 18% nitrogen, 8% phosphorus and 18% potassium. The average air temperature was 24° C.

Color designations were made according to The Royal Horticultural Society Colour Chart published by The Royal Horticultural Society of London, England.

Origin: Japan.
Parentage: A vegetative sport from variety 'Summer Baby Orange' (not patented).
Classification:
- *Family.*—Portulacaceae.
- *Genus.*—Portulaca.
- *Species.*—*oleracea.*
- *Commercial.*—Portulaca/Purslane 'Kakegawa CY1'.

Plant:
- *Growth habit.*—Prostrate.
- *Plant height.*—23.0 cm.
- *Spread.*—85 cm (in a six-inch pot).
- *Life cycle.*—Perennial.
- *Time to produce a rooted cutting.*—2 weeks.
- *Time to bloom from propagation.*—6–8 weeks.
- *Time to produce a rooted cutting.*—Vegetative cuttings root in 7–10 days after sticking into a rooting medium like a peat moss based mix; the cuttings will form roots without the use of overhead mist.
- *Flowering season.*—Spring to Fall.

*Flowering requirements.*—Flowers year round at temperatures of 24°–35° C.; day neutral light requirements.

*Temperature.*—Will not tolerate temperatures below 7° C.

Stem:

*Color.*—Yellowish green (144C).

*Anthocyanin.*—RHS 178B (greyed-red).

*Pubescence.*—Glabrous.

*Stem description.*—Round, slightly rough with lateral ridges.

*Diameter.*—5.0 mm.

*Branching.*—Abundant.

*Length of internode.*—3.0–3.5 cm.

Leaf:

*Apex.*—Acute.

*Base.*—Rounded.

*Arrangement.*—Alternate; leaves appear whorled towards the apex where internodes are not elongated.

*Leaf color.*—Upper surface RHS 137C (green); lower surface RHS 138C (green).

*Anthocyanin.*—RHS 178B (greyed-red).

*Margin.*—Entire.

*Length* (*average*).—2.0 cm.

*Width* (*average*)—1.5 cm.

*Shape.*—Oblong.

*Thickness.*—1.0 mm.

*Texture.*—Smooth.

*Petiole color.*—RHS N144D (yellow-green).

*Petiole length.*—2.0 mm.

*Petiole diameter.*—2.0–3.0 mm.

Flower:

*Calyx.*—2 sepals; 8.0×8.0 mm; free.

*Sepal shape.*—Elliptic.

*Sepal texture.*—Smooth.

*Sepal margin.*—Entire, slightly sinuate.

*Sepal apex shape.*—Cuspidate.

*Sepal color.*—Base is RHS 146C (yellow-green); dark opaque pink mixed with green toward the tip (RHS 51B).

*Corolla.*—5 petals outer whorl; numerous inner; approximately 72 petals per flower; free.

*Flower diameter.*—3.5 cm.

*Bud color.*—RHS 138B (green).

*Bud shape.*—Round and pointed at the top.

*Bud size.*—Length 1.1–1.2 cm; diameter 8 mm.

*Bud surface.*—Shiny.

*Duration of flower life.*—One day.

*Flowering habit.*—Determinate.

*Inflorescence type.*—Solitary, sessile.

*Stamens.*—None.

*Style.*—None.

*Petal shape.*—Double-lobed; obovate.

*Petal margin.*—Sinuate.

*Petal apex shape.*—Cuspidate.

*Petal surface.*—Smooth and soft.

*Petal size.*—5 outer petals 2.0×1.2 cm (l×w); numerous center petals 1.2 cm×3.0–4.0 mm (l×w).

*Petal color.*—Upper surface of petal margin the color is RHS 2A (yellow) that blends with and changes to 34C (orange) toward the base of the petal; lower surface of petal margin the color is RHS 2A (yellow) that blends with and changes to RHS 51C (red) toward the base of the; base of petal upper surface RHS 34A (orange-red); lower surface RHS 34A (orange-red).

*Produces seeds.*—No.

*Habit.*—The flowers bloom during midmorning and close at night. Each flower blooms only once and are produced throughout the growing season. The plants produce flowers regardless of day length; the plants are day neutral. Plants can have 40 to 50 open flowers at one time and have no fragrance.

*Hardiness.*—Plant is heat tolerant; thrives in heat and humidity; plant is not cold tolerant or below 7° C.

Disease and Insect Resistance

No unusual susceptibility to diseases or insects have been observed.

Comparison with Other Known Varieties

'Kakegawa CY1' is most similar to the variety 'Summer Baby Orange' (not patented). Both plants have similar foliage, a prostrate habit and semi-doubled petals. 'Kakegawa CY1' differs from 'Summer Baby Orange' in flower color.

We claim:

1. A new and distinct Portulaca plant as shown and described herein.

* * * * *